United States Patent
Nezhat

[19]

[11] Patent Number: 6,162,220
[45] Date of Patent: Dec. 19, 2000

[54] BIPOLAR SURGICAL INSTRUMENTS HAVING FOCUSED ELECTRICAL FIELDS

[75] Inventor: Camran Nezhat, Woodside, Calif.

[73] Assignee: Perfect Surgical Techniques, Inc., Palo Alto, Calif.

[21] Appl. No.: 09/303,007

[22] Filed: Apr. 30, 1999

Related U.S. Application Data

[63] Continuation-in-part of application No. 09/071,689, May 1, 1998, Pat. No. 6,030,384.

[51] Int. Cl.⁷ .................................................. A61B 18/18
[52] U.S. Cl. ............................................. 606/48; 606/51
[58] Field of Search .......................................... 606/41–52

[56] References Cited

U.S. PATENT DOCUMENTS

| | | |
|---|---|---|
| 3,920,021 | 11/1975 | Hiltebrandt . |
| 4,016,886 | 4/1977 | Doss et al. . |
| 4,041,952 | 8/1977 | Morrison, Jr. et al. . |
| 4,043,342 | 8/1977 | Morrison, Jr. . |
| 4,671,274 | 6/1987 | Sorochenko . |
| 5,098,431 | 3/1992 | Rydell . |
| 5,151,102 | 9/1992 | Kamiyama et al. . |
| 5,207,691 | 5/1993 | Nardella . |
| 5,217,030 | 6/1993 | Yoon . |
| 5,217,460 | 6/1993 | Knoepfler . |
| 5,267,998 | 12/1993 | Hagen . |
| 5,269,780 | 12/1993 | Roos . |
| 5,269,782 | 12/1993 | Sutter . |
| 5,281,216 | 1/1994 | Klicek . |
| 5,282,799 | 2/1994 | Rydell . |
| 5,290,287 | 3/1994 | Boebel et al. . |
| 5,295,990 | 3/1994 | Levin . |
| 5,300,087 | 4/1994 | Knoepfler . |
| 5,324,289 | 6/1994 | Eggers . |
| 5,330,471 | 7/1994 | Eggers . |
| 5,336,229 | 8/1994 | Noda . |
| 5,342,381 | 8/1994 | Tidemand . |
| 5,352,223 | 10/1994 | McBrayer et al. . |
| 5,352,235 | 10/1994 | Koros et al. . |
| 5,356,408 | 10/1994 | Rydell . |
| 5,383,876 | 1/1995 | Nardella . |
| 5,391,166 | 2/1995 | Eggers . |
| 5,395,369 | 3/1995 | McBrayer et al. . |
| 5,396,900 | 3/1995 | Slater et al. . |

(List continued on next page.)

FOREIGN PATENT DOCUMENTS

| | | |
|---|---|---|
| 598149 | 7/1925 | France . |
| 197711 | 11/1977 | U.S.S.R. . |

*Primary Examiner*—John P. Leubecker
*Assistant Examiner*—Roy Gibson
*Attorney, Agent, or Firm*—Townsend and Townsend and Crew LLP

[57] ABSTRACT

A bipolar surgical device includes a pair of actuable jaws. A first electrode member which optionally includes a line of electrically coupled tissue-penetrating elements is formed on one of the jaws, and a second electrode member which optionally includes a line of electrically coupled tissue-penetrating elements is formed on the same or the other jaw. The electrode members are laterally spaced-apart and arranged in a parallel, usually linear manner so that the lateral distance therebetween remains generally constant. In operation, tissue may be grasped between the jaws so that the electrode members contact and/or the tissue-penetrating elements enter into the tissue. By energizing the electrode members at opposite polarities using a high frequency energy source, tissue between the jaws will be heated, coagulated, and/or necrosed, while heating of tissue outside of the lines will be minimized.

40 Claims, 11 Drawing Sheets

U.S. PATENT DOCUMENTS

| | | |
|---|---|---|
| 5,403,312 | 4/1995 | Yates et al. . |
| 5,417,687 | 5/1995 | Nardella et al. . |
| 5,423,814 | 6/1995 | Zhu et al. . |
| 5,443,463 | 8/1995 | Stern et al. . |
| 5,445,638 | 8/1995 | Rydell et al. . |
| 5,456,684 | 10/1995 | Schmidt et al. . |
| 5,458,598 | 10/1995 | Feinberg et al. . |
| 5,462,546 | 10/1995 | Rydell . |
| 5,469,312 | 11/1995 | Klicek . |
| 5,482,054 | 1/1996 | Slater et al. . |
| 5,484,435 | 1/1996 | Fleenor et al. . |
| 5,484,436 | 1/1996 | Eggers et al. . |
| 5,496,317 | 3/1996 | Goble et al. . |
| 5,514,134 | 5/1996 | Rydell et al. . |
| 5,527,313 | 6/1996 | Scott et al. . |
| 5,531,744 | 7/1996 | Nardella et al. . |
| 5,540,684 | 7/1996 | Hassler, Jr. . |
| 5,540,685 | 7/1996 | Parins et al. . |
| 5,542,945 | 8/1996 | Fritzsch . |
| 5,549,606 | 8/1996 | McBrayer et al. . |
| 5,558,100 | 9/1996 | Cox . |
| 5,558,671 | 9/1996 | Yates . |
| 5,569,243 | 10/1996 | Kortenbach et al. . |
| 5,573,535 | 11/1996 | Koros et al. . |
| 5,578,052 | 11/1996 | Viklund . |
| 5,599,350 | 2/1997 | Schulze et al. . |
| 5,603,711 | 2/1997 | Parins et al. . |
| 5,624,452 | 4/1997 | Yates . |
| 5,626,578 | 5/1997 | Tihon . |
| 5,637,110 | 6/1997 | Pennybacker et al. . |
| 5,637,111 | 6/1997 | Sutcu et al. . |
| 5,658,281 | 8/1997 | Heard . |
| 5,662,680 | 9/1997 | Desai . |
| 5,665,085 | 9/1997 | Nardella . |
| 5,665,100 | 9/1997 | Yoon . |
| 5,667,526 | 9/1997 | Levin . |
| 5,669,907 | 9/1997 | Platt, Jr. et al. . |
| 5,674,184 | 10/1997 | Hassler, Jr. . |
| 5,674,220 | 10/1997 | Fox et al. . |
| 5,681,282 | 10/1997 | Eggers et al. . |
| 5,683,385 | 11/1997 | Kortenbach et al. . |
| 5,683,388 | 11/1997 | Slater . |
| 5,688,270 | 11/1997 | Yates et al. . |
| 5,693,051 | 12/1997 | Schulze et al. . |
| 5,697,949 | 12/1997 | Giurtino et al. . |
| 5,700,261 | 12/1997 | Brinkerhoff . |
| 5,702,390 | 12/1997 | Austin et al. . |
| 5,707,369 | 1/1998 | Vaiterkunas et al. . |
| 5,709,680 | 1/1998 | Yates et al. . |
| 5,713,896 | 2/1998 | Nardella . |
| 5,718,703 | 2/1998 | Chin . |
| 5,733,283 | 3/1998 | Malis et al. . |
| 5,735,848 | 4/1998 | Yates et al. . |
| 5,735,849 | 4/1998 | Baden et al. . |
| 5,741,285 | 4/1998 | McBrayer et al. . |
| 5,743,906 | 4/1998 | Parins et al. . |
| 5,755,717 | 5/1998 | Yates et al. . |
| 5,833,690 | 11/1998 | Yates et al. ............................... 606/52 |
| 5,891,142 | 4/1999 | Eggers et al. . |

BIPOLAR SURGICAL INSTRUMENTS HAVING FOCUSED ELECTRICAL FIELDS

This application is a continuation-in-part application Ser. No. 09/071,689, filed on May 1, 1998, now U.S. Pat. No. 6,030,384, the full disclosure of which is incorporated herein by reference.

BACKGROUND OF THE INVENTION

1. Field of the Invention

The present invention relates generally to medical devices and methods. More particularly, the present invention relates to the structure and use of bipolar forceps and other instruments for coagulating, cutting, and necrosing tissue.

Electrosurgery refers broadly to a class of medical procedures which rely on the application of high frequency electrical energy, usually radiofrequency energy, to patient tissue to achieve a number of possible effects, such as cutting, coagulation, hyperthermia, necrosis, and the like. Of particular interest to the present invention, bipolar electrosurgical devices rely on contacting electrodes of different polarity in close proximity to each other against or into tissue. For example, bipolar forceps 100 (FIGS. 1 and 2) have been used for cutting and coagulating tissue, where the opposed jaws 102 and 104 of the forceps are connected to different poles of an electrosurgical power supply. The high frequency electrical current thus flows from one jaw to the other through the tissue present therebetween. Use of such bipolar forceps is effective for a number of purposes and advantageous in that its effect is generally limited to the tissue held between the jaws. Heating, however, is not totally limited to such intermediate tissue, and in some instances heating of adjacent tissues can be problematic. Such heating occurs because the current flows not only between the jaws but also laterally outward, as shown by flux lines F in FIG. 1B.

Various improvements to bipolar forceps have been proposed. For example, the placement of pins or other tissue-penetrating elements onto the tissue-engaging surface(s) of either or both jaws has been suggested for a variety of purposes. Regardless of the intended purpose, the placement of tissue-penetrating elements on the jaw(s) can marginally focus the current density and somewhat lessen heating of adjacent tissues. Such prior designs employing tissue-penetrating elements, however, still cause unwanted heating of adjacent tissues in at least certain circumstances.

A second problem with conventional bipolar forceps is limited power delivery. With conventional forceps, jaws having a length of about 20 mm and a width of about 5 mm can usually deliver only 25 W of power without causing charring of the tissue. Charring greatly increases electrical resistance through the tissue and can result in premature termination of the treatment. With such a low power level, the time to fully coagulate the tissue can be excessive.

It would therefore be desirable to provide still further improved bipolar forceps and other electrosurgical device designs. In particular, it would be desirable to provide bipolar forceps which provide a very high degree of focused heating, i.e., provide heating of tissue between the jaws with minimized heating of tissue adjacent to the jaws. It would be further desirable to provide bipolar forceps which can deliver higher current flows and densities to the tissue being treated without charring the tissue and terminating the current flow. Such device designs should be relatively simple and easy to fabricate. The devices and methods should be compatible with conventional electrosurgical power supplies and usable in a wide variety of procedures, including cutting, coagulation, and necrosis, where the localized and specific heating of patient tissues is desired. At least some of these objectives will be met by the invention described hereinafter.

2. Description of the Background Art

Bipolar forceps having penetrating elements on opposed jaws thereof are described in U.S. Pat. Nos. 5,527,313 and 5,217,460; Soviet Union Patent Publication SU 197711; and French Patent No. 598,149. Bipolar electrosurgical instruments having laterally spaced-apart electrodes on opposed jaws are described in U.S. Pat. Nos. 5,833,690; 5,702,390; 5,688,270; and 5,403,312. A blood vessel coagulation device having electrode arrays on opposed jaws of forceps is described in U.S. Pat. No. 5,151,102. Other bipolar electrosurgical devices are described in U.S. Pat. Nos. 5,797,941; 5,665,085; 5,662,680; 5,582,611; 5,445,638; 5,441,499; 5,383,876; 5,403,312; 5,098,431; and 4,043,342. A radiofrequency tumor heating device comprising parallel electrode arrays of opposite polarity is described in U.S. Pat. No. 4,016,886.

SUMMARY OF THE INVENTION

The present invention provides improved bipolar surgical instruments, such as forceps, graspers, or the like, which comprise a pair of opposed jaws at the distal end of a shaft. The present invention is directed at a unique electrode configuration on either or both of the jaws which will provide improved current focussing characteristics and lessened heating of adjacent tissues. In particular, electrode members on either or both of the jaws will be laterally spaced apart from each other when the jaws are closed so that current will flow from one electrode to the other with minimum current flow outside of the region defined between the electrodes. Optionally, a pair of electrodes can be provided on each jaw with a positive and negative electrode on one jaw and a positive and negative electrode on the other jaw, with the two positive electrodes and the two negative electrodes being aligned with each other when the jaws are closed to define the desired focussed current flow.

At least one of the electrode members will include tissue-penetrating elements. Usually a first line of electrically coupled tissue-penetrating elements will be provided on a first electrode member, and a second line of electrically coupled tissue-penetrating elements will be provided on a second electrode member. Third and fourth lines of electrically coupled tissue-penetrating elements will preferably be provided when third and fourth electrode members are provided on the instrument. The first and second lines (and optionally third and fourth lines) of tissue-penetrating elements will be electrically isolated from each other to permit energization in a bipolar manner, i.e., each line of electrically coupled tissue-penetrating elements may be separately connected to the opposite pole of a conventional electrosurgical power supply. The shaft includes or comprises an actuating mechanism for moving the jaws between opened and closed configurations, where the lines of tissue-penetrating elements lie parallel to and spaced-apart from each other when the jaws are closed. In this way, the jaws can be closed on a target tissue structure, such as a fallopian tube, artery, vein, and the like, in order to penetrate the lines of elements into the tissue. By then applying high frequency electrical energy to the lines in a bipolar manner, current flux will be focused to within that portion of the tissue which lies between the adjacent lines, with minimum heating of tissue outside of the parallel lines. Usually, but not necessarily, the lines will both be straight. Alternatively, the lines could be nonlinear, e.g., curved, serpentine, zig-zag, or the like, so long as the patterns are similar and the lateral spacing between adjacent points on the lines remains substantially constant. Preferably, the spacing between the adjacent lines of tissue-penetrating elements will be in the range from 0.5 mm to 10 mm, more preferably from 2 mm to 5 mm.

Preferably, at least some of the tissue-penetrating elements on the electrode member(s) will be retractable relative to a surface of the jaw upon which they are mounted. Usually, the tissue-penetrating elements will be arranged to reciprocate in and out of either or both of the jaws so that the jaws can be clamped over opposed surfaces of a target tissue region or mass with the elements retracted and the elements then penetrated into the tissue while the tissue remains clamped. In some instances, lines of reciprocating tissue-penetrating elements will define at least two and sometimes all of the electrode members. In other instances, they will form only one of the electrode members and/or they will be combined together with one or more elongate surface electrodes which engage but do not penetrate into the tissue.

The lines of tissue-penetrating elements may be on the same jaw or on different jaws. When the lines are on the same jaw, it is necessary to provide insulation so that each line is electrically isolated from the other, while the plurality of tissue-penetrating elements in an individual line remain electrically coupled. Electrical conductors will be provided within the shaft in order to permit attachment of each line to opposite polarity connections on an electrosurgical power supply. When present on different jaws, the lines of tissue-penetrating elements may be isolated from each other by maintaining appropriate electrical isolation between the jaws and/or at either or both ends of the tissue-penetrating elements.

The tissue-penetrating elements may have a wide variety of different configurations. Most commonly, they will be in the form of a pin or other rod-like tissue-penetrating electrode, usually having a sharpened distal end to facilitate penetration into tissue. Alternatively, an appropriate cutting current could be applied to the electrodes in order to facilitate tissue penetration while the jaws are being closed. Each line of tissue-penetrating elements may contain from 3 to 50 individual elements, usually from 6 to 25. The elements may extend over a length on the jaw(s) in the range from 1 mm to 50 mm, usually from 5 mm to 25 mm, with spacing between individual elements being in the range from 0.25 mm to 5 mm, usually from 0.5 mm to 2 mm. The distance between adjacent lines of tissue penetrating elements will usually be in the range from 0.5 mm to 10 mm, usually from 2 mm to 5 mm. The height of the tissue-penetrating elements (corresponding to the depth of tissue penetration) will usually be in the range from 1 mm to 10 mm, preferably from 2 mm to 5 mm, while the diameter of the elements will typically from 0.1 mm to 2 mm, usually from 0.5 mm to 1 mm.

Optionally, either or both of the jaws may be perforated or otherwise provided with passages in order to permit the release of steam which is a byproduct of tissue heating. A mechanism will be provided on the shaft for actuating the jaws, i.e., opening and closing the jaws so that they may grasp tissue therebetween. Exemplary actuating mechanisms include scissors, camming mechanisms, linear/pivot actuators, and the like.

In several specific embodiments, the bipolar surgical instrument of the present invention will comprise a shaft and a pair of opposed jaws, as generally described above. At least two laterally spaced-apart elongate surface electrodes will be positioned on the jaws (either on the same jaw or opposed surfaces of the two jaws). At least a first line of tissue-penetrating elements will be disposed on at least one of the jaws so that the line of electrodes is arranged to lie between the two surface electrodes when the jaws are closed. Preferably, the line of tissue-penetrating electrodes will be retractable or reciprocatable relative to the surface of the jaw in which it is mounted. Usually, the tissue-penetrating elements will reciprocate in and out of the jaw itself. Alternatively, a surface of the jaw can be arranged to move upwardly and downwardly over the tissue-penetrating elements (typically in the form of pins, needles, or other self-penetrating rods) in order to cover and uncover the elements. In addition to protecting the tissue-penetrating elements and facilitating grasping of tissue (without the tissue-penetrating elements interfering when they are retracted), reciprocation of the elements has the additional advantage of cleaning the tissue-penetrating elements during use. Frequently, charred tissue coagulated blood and/or other debris may foul the tissue-penetrating elements reducing their ability to effectively deliver high frequency electrical energy to the tissue. Reciprocation of the elements within the structure of the instrument will tend to shear debris from the surfaces of the tissue-penetrating elements (electrodes) to decrease surface resistance and impedance. Optionally, the instrument may include at least a second line of tissue-penetrating elements on either or both of the jaws. Usually, the first and second lines of the tissue-penetrating elements will be on the same jaw and will be spaced between the two laterally spaced-apart elongate surface electrodes. In this way, the surface electrodes define outer lateral edges to the region which is being treated and necrosed. Since these outer electrodes do not penetrate tissue, they will have less of a tendency to cause bleeding after treatment. It has been found that penetration of the tissue-penetrating elements into larger blood vessels can result in bleeding, even if the site is cauterized and necrosed by the device. By defining the outer edge of the treated region with non-penetrating electrodes or other elements, the risk of bleeding is substantially decreased.

In a still further prefenred aspect of the invention, a knife, blade, or other tissue-cutting structure is disposed on the instrument to cut along the line between the first and second lines of tissue-penetrating elements. In this way, the jaws can be clamped on tissue, the tissue-penetrating elements penetrated into the tissue, the tissue treated electrosurgically, and the tissue then cut between the two necrosed tissue regions. By defining the outer region of tissue necrosis with the non-penetrating electrode elements, the risk of bleeding is greatly reduced.

Methods according to the present invention rely on grasping tissue between a first jaw and a second jaw. A high frequency energy is then applied between a first line of tissue-penetrating elements on one of the jaws and a second line of tissue-penetrating elements on the same or a different jaw. The tissue-penetrating element lines are parallel and spaced-apart from each other, generally as described above. The high frequency energy will preferably be applied to the tissue at a level and for a time sufficient to necrose substantially all tissue between the lines without causing substantial damage to other tissue, i.e., tissue outside of the lines. Typically, the high frequency energy will be applied at a frequency in the range from 100 kHz to 2 MHz, preferably from 400 kHz to 500 kHz. The energy will be applied at a power from 25 W to 250 W, preferably from 50 W to 150 W, and for a time in the range from 5 seconds to 5 minutes, usually from 10 seconds to 1 minute.

In a more specific aspect of the method of the present invention, a tissue region is contacted with at least two laterally spaced-apart elongate surface electrodes. At least a first line of tissue-penetrating elements is penetrated through a surface of the tissue region located between the laterally spaced-apart surface electrodes. Bipolar high frequency electrical energy is then applied between the surface electrodes (at one plurality) and the tissue-penetrating elements (at the other plurality) in order to treat and usually necrose tissue within the boundary regions defined by the laterally spaced-apart surface electrodes. Optionally, at least a second line of tissue-penetrating elements will be penetrated through the tissue surface and energized at the same plurality as the first line of tissue-penetrating elements. The contacting and penetrating steps may be performed sequentially or simultaneously, preferably being performed sequentially so that the tissue may first be captured before penetrating the tissue-penetrating elements therein.

DESCRIPTION OF THE SPECIFIC EMBODIMENTS

Figure 1A:
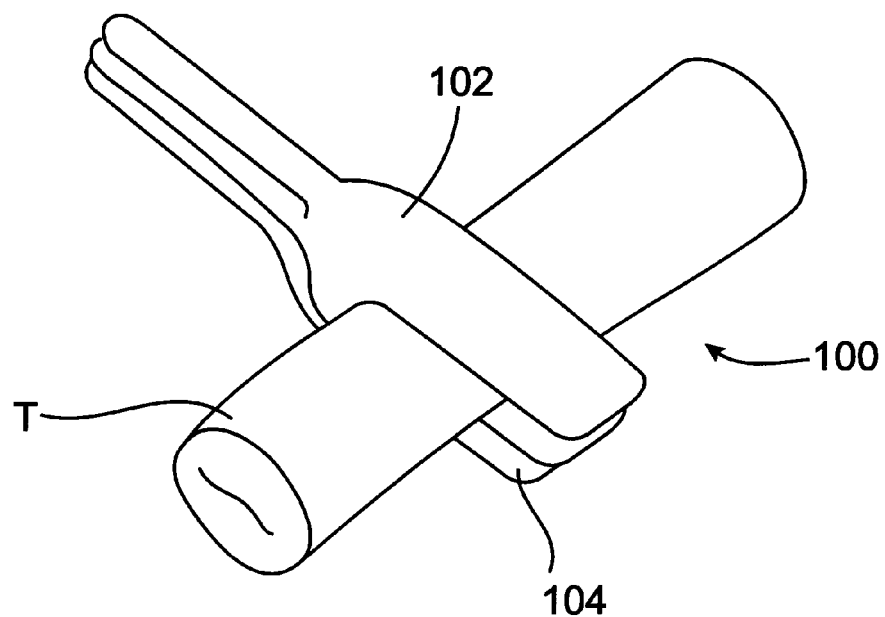
FIGS. 1A and 1B illustrate use of conventional bipolar forceps for coagulating a tubular structure in the body.

According to the present invention, bipolar surgical instruments will include at least two and up to four or more laterally spaced-apart electrode members disposed on a pair of actuable jaws. By properly positioning the electrode members relative to each other, radiofrequency energy applied to tissue disposed between the jaws can be focused within a well-defined region between the electrode members. In contrast to prior art devices and methods, where electrodes of opposite polarity are generally engaged against directly opposed tissue surfaces, the present invention will position at least one positive electrode and at least one negative electrode on and/or into laterally spaced-apart sites on opposed tissue surfaces.

The electrode members may be configured in a wide variety of patterns and designs, some of which are illustrated in FIGS. 2A–2E. Most simply, one jaw 200 may carry a first electrode member 202 which is laterally spaced-apart from a second electrode member 204, where the electrode members are connectable to opposite poles of a power supply. An opposed jaw 206 may be free from electrodes of any sort. The jaws 200 and 206 will be actuable, as described in more detail hereinafter, so the tissue may be grasped between two opposed tissue-engaging surfaces 208 and 210. When tissue is grabbed between the jaws 200 and 206, current flow will be generally limited to between the electrode members 202 and 204.

Figure 2A:
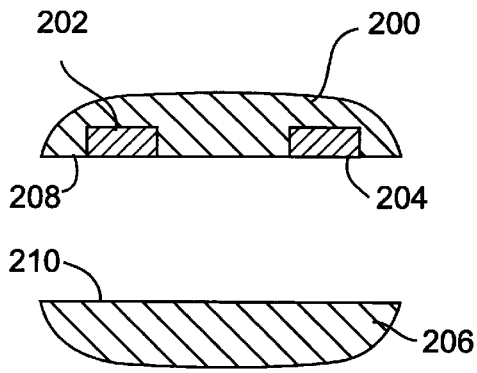
FIGS. 2A–2F illustrate a plurality of alternative electrode configurations according to the present invention.
Figure 2B:
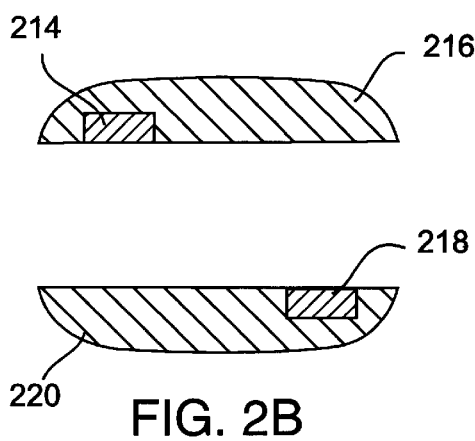

While the electrode member configuration of FIG. 2A is functional, the current flow pattern between the electrodes can be improved by having a first electrode member 214 on a first jaw 216 and a second electrode member 218 on a second jaw 220 as illustrated in FIG. 2B. As with the configuration of FIG. 2A, the electrode members 214 and 218 of FIG. 2B will generally limit current flow so that it does not extend significantly to tissue outside the lateral boundaries of the jaws 216 and 220. By placing the electrode members 214 and 218 on opposed jaws, enhanced current flow through the tissue may be achieved.

Figure 2C:
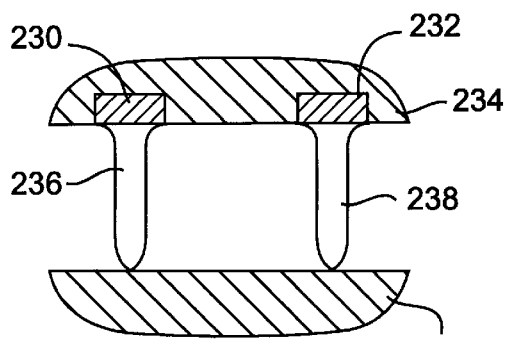

A further alternative improved configuration of the electrode members according to the present invention is illustrated in FIG. 2C. First electrode member 230 and second electrode member 232 are each carried on a first jaw 234, in a manner similar to the embodiment of FIG. 2A. The electrode members 230 and 232, however, each include a line of tissue-penetrating elements thereon. The electrode members 202 and 204 in FIG. 2A are generally linear electrodes having a width and length within the ranges set forth above. Such electrodes will form a flat contact or interface with the tissue which is engaged between the jaws 200 and 206. By providing tissue-penetrating elements 236 and 238, as illustrated in FIG. 2C, two advantages are achieved. First, the total electrode area in contact with the tissue can be greatly enhanced, typically from two-fold to 10-fold, or greater. Moreover, by extending the electrode "boundaries" into the tissue, the ability to achieve uniform current flux within the tissue is improved and the containment of that current flux within the target region is also enhanced. The embodiment of FIG. 2C will include an opposed jaw 240 which is free from electrodes.

Figure 2D:
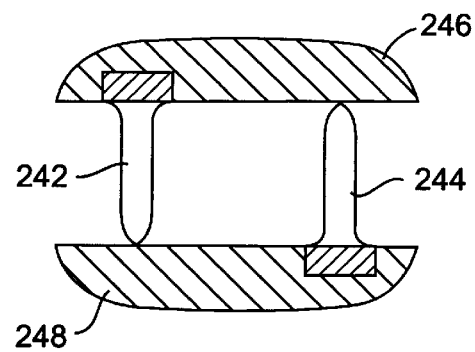

A slightly modified configuration for tissue-penetrating elements 242 and 244 is illustrated in FIG. 2D. Instead of carrying both lines of tissue-penetrating elements 242 and 244 on a single jaw, the first line 242 is carried on an upper jaw 246 and the second line 244 is carried on a lower jaw 248. The advantages regarding increased electrode area and current flux containment, however, are generally comparable to those achieved with the embodiment of FIG. 2C.

Figure 2E:
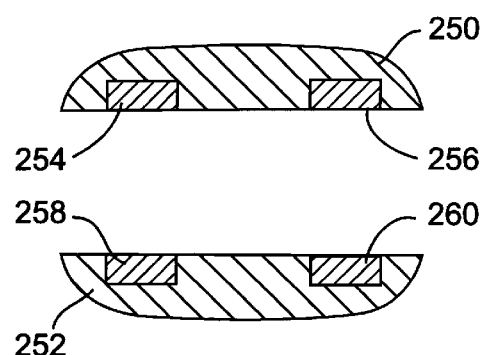

Yet another alternative for the electrode member configuration is illustrated in FIG. 2E. Jaws 250 and 252 each carry pairs of laterally spaced-apart members 254, 256, 258 and 260. The electrode members can be adapted for connection to a power supply so that laterally spaced-apart pairs of electrodes will have opposite polarity when the instrument is powered. For example, electrodes 254 and 258 may have a first polarity while electrodes 256 and 260 may have a second polarity. Alternatively, but less preferably, electrodes 254 and 260 may have a first polarity while electrodes 258 and 256 may have a second polarity. The latter configuration will be generally less effective at containing current flow than the former configuration since pairs of oppositely energized electrodes will directly oppose each other when the instrument is engaged against tissue.

Figure 2F:
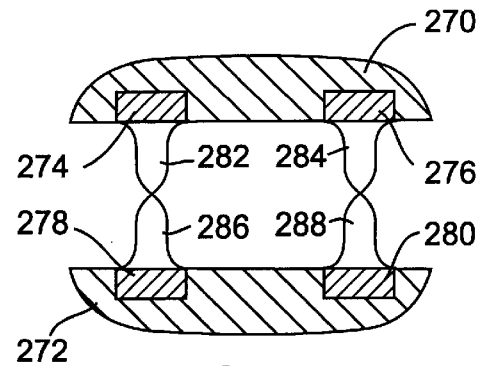

Yet another electrode configuration is illustrated in FIG. 2F. There, each jaw 270 and 272 carries a pair of electrode members 274, 276, 278, 280. Each of the electrode members, in turn, carries a line of tissue-penetrating elements 282, 284, 286, 288. The tissue-penetrating elements are arranged so that their distal tips will engage each other when the jaws 270 and 272 are closed together. Opposed pairs of electrode members 274/278 and 276/280 will have the same polarity, i.e., the laterally spaced-apart pairs will be of opposite polarity. In many ways, the operation of the embodiment of FIG. 2F will be the same as that of both FIG. 2C and FIG. 2D. The embodiment of FIG. 2F may also be modified by axially spacing apart the opposed penetrating elements 282/286 and 284/288 so that the elements penetrate fully to the opposed jaw 270 or 272. A variety of other electrode modifications will also be possible within the scope and spirit of the present invention.

Figure 3A:
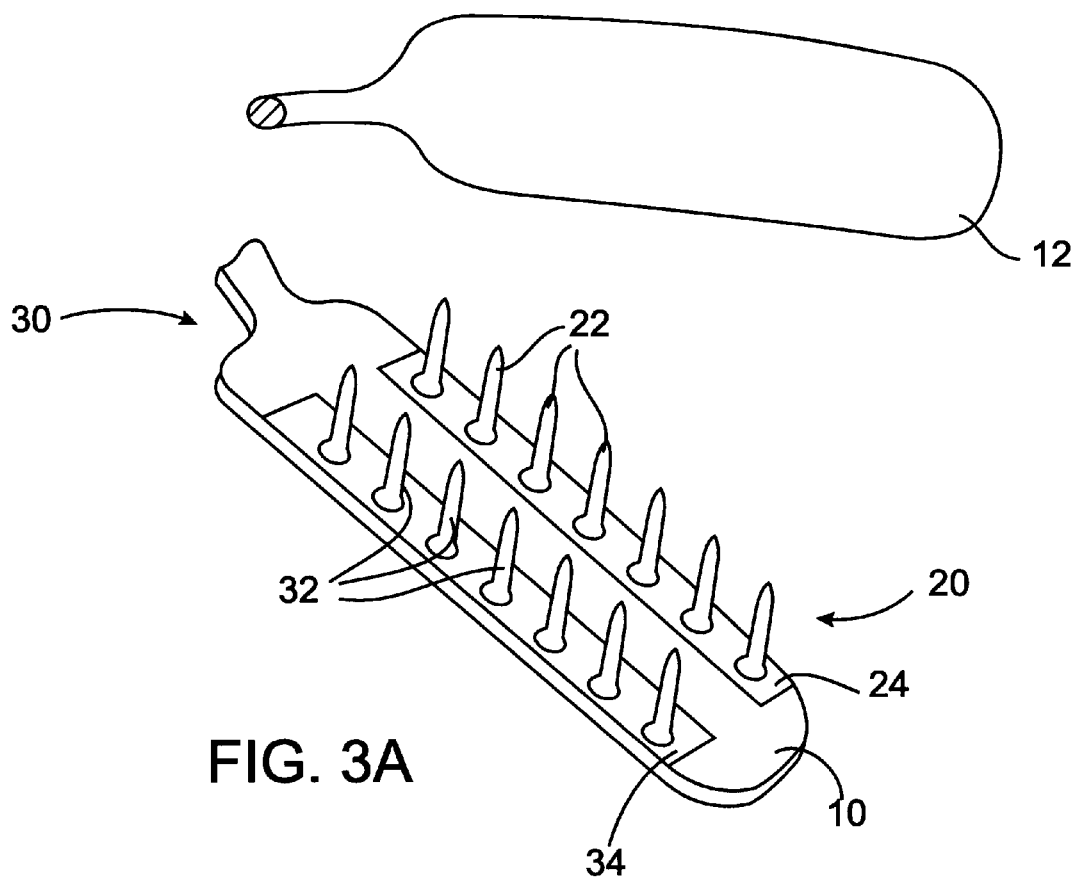
FIG. 3A is a perspective view of a pair of actuable jaws carrying two lines of electrically coupled tissue-penetrating elements in accordance with the principles of the present invention.
Figure 3B:
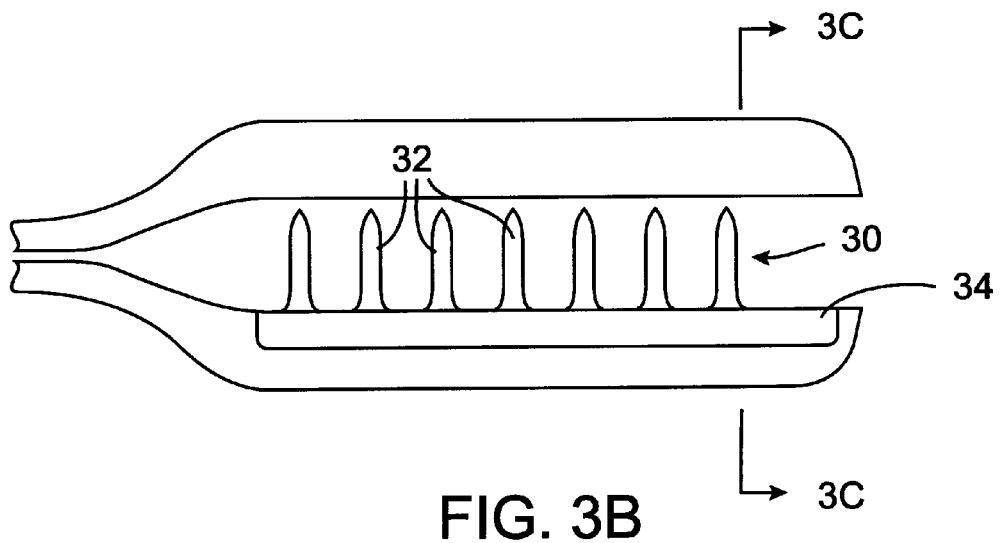
FIG. 3B is a side, elevational view of the jaws of FIG. 1, shown with the jaws closed.
Figure 3C:
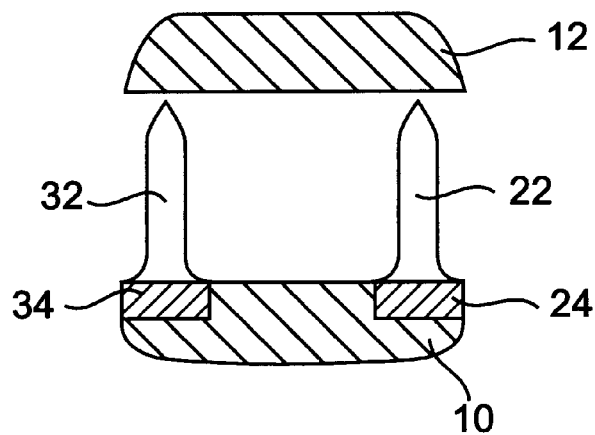
FIG. 3C is a cross-sectional view taken along line 3—3 of FIG. 2.

Referring now to FIGS. 3A–3C, a first exemplary pair of jaws 10 and 12 which may be utilized for grasping tissue and applying high frequency energy according to the methods of the present invention will be described. The jaws 10 and 12 will be actuable or reciprocatable in a manner conventional for forceps, graspers, and other similar types of medical devices. Specific shaft designs which provide for such actuation will be described hereinafter in connection with FIGS. 5–7.

A first line 20 comprising seven tissue-penetrating pins 22 is disposed on one side of the lower jaw 10 and a second line 30 of tissue-penetrating pins 32 is disposed on the other side of the lower jaw. The first line 20 of pins 22 is electrically coupled by an electrically conductive strip 24 into which the pins are attached. Similarly, a second electrically conductive strip 34 is disposed on the other side of the jaw and electrically couples the second line 30 of pins 32. Each of the electrically conductive strips 24 and 32 will be attached to conductors (not shown) which extend proximally down the shaft of the device and which provide for electrical attachment of the lines 20 and 30 to a conventional electrosurgical power supply.

The electrically conductive strips 24 and 34 will be electrically isolated from each other. For example, the strips 24 and 34 may be imbedded in an insulating material, such as a ceramic, plastic, or the like. Alternatively, an insulating layer may be formed around the strips 24 so that they are electrically isolated from the lower jaw 10. The upper jaw 12 may also be formed from a ceramic or other electrically insulating material to assure that the pins 22 and 32 are not shorted by contact with the upper jaw. The pins 22 and 32 and strips 24 and 34 will be formed from an electrically conductive material, typically a metal such as stainless steel, gold, silver, or the like. The dimensions, number, spacing, and other characteristics of the pins 22 and 32 will be within the ranges set forth above. While shown in a straight line, the pins 22 and 32 could also be arranged in the other patterns set forth above.

Figure 4:
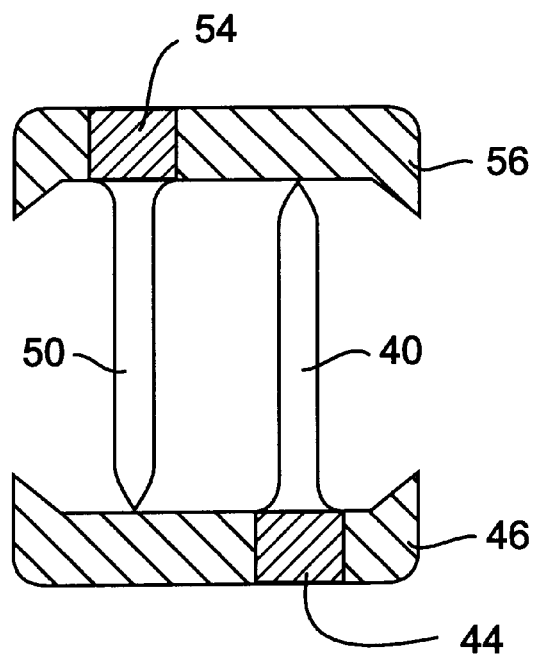
FIG. 4 is an alternative cross-sectional view of a pair of jaws constructed in accordance with the principles of the present invention.

The embodiment of FIGS. 3A–3C shows both lines 20 and 30 of tissue-penetrating elements 22 and 32 being connected to the same jaw. The present invention would also cover embodiments where the lines of tissue-penetrating elements are connected to opposite jaws, as shown in FIG. 4. There, a first line of pins 40 are mounted within a conductive strip 44 in a lower jaw 46, while a second line of tissue-penetrating elements 50 are mounted in an electrically conductive strip 54 in an upper jaw 56. The individual tissue-penetrating elements 40 and 50 are thus coupled to each other within each line, but the two lines are electrically isolated, so that the result is a pair of electrically isolated lines of tissue-penetrating elements, as with the first embodiment.

Figure 5:
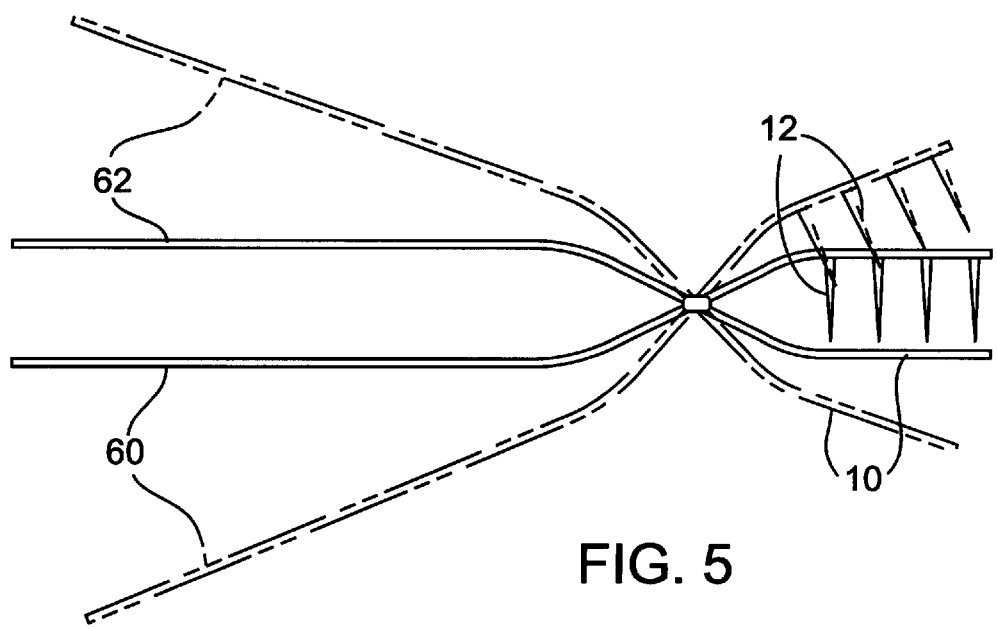
FIG. 5 illustrates a scissors-type actuating mechanism that can be used with the jaws of FIG. 1.
Figure 6:
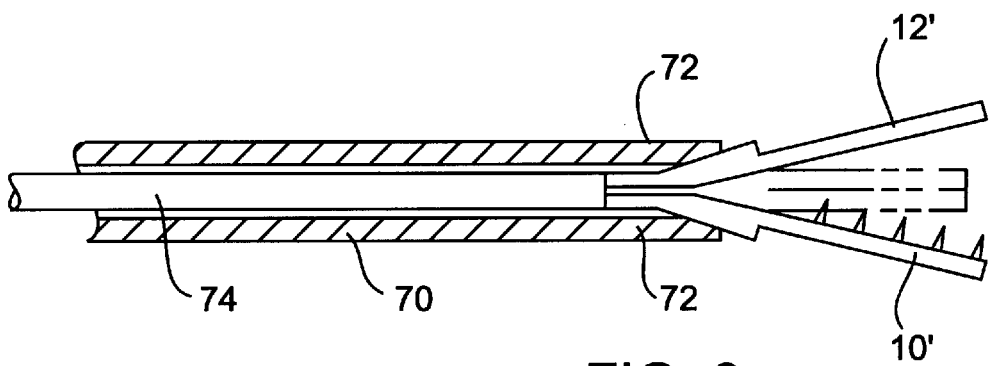
FIG. 6 illustrates a pair of resiliently-mounted jaws that can be opened and closed with a cam surface, where the jaws incorporate tissue-penetrating elements according to the principles of the present invention.
Figure 7:
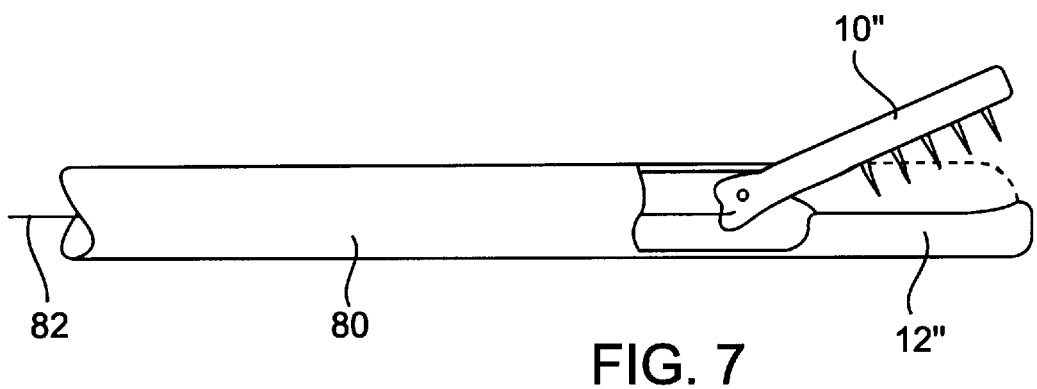
FIG. 7 illustrates an alternative jaw actuating mechanism which may be utilized in the devices of the present invention.

Referring now to FIGS. 5–7, the present invention can rely on virtually any jaw-actuating mechanism of a type utilized in medical devices. For example, the mechanism can be a simple scissors mechanism, as shown in FIG. 5, where the jaws 10 and 12 are pivotally connected to actuating levers 60 and 62. Opening and closing of the levers 60 and 62 will open and close the jaws in a conventional manner.

Jaws 10' and 12' can also be mounted within a hollow tube 70 having cam surfaces 72 formed at its distal end. The jaws 10' and 12' are resiliently mounted on a rod 74 so that the jaws may be axially translated relative to the cam surfaces 72 to open the jaws (as shown in full line) and close the jaws (as shown in broken line) in FIG. 6.

As a third common alternative, jaws 10" and 12" may be formed at the distal end of a tubular actuator 80. The jaw 10" which is free from tissue-penetrating elements is integrally formed at the end of the tube 80. The moveable jaw 10" having the tissue-penetrating elements is pivotally attached and is actuated by a rod 74 or cable 82 extending to a proximal end of the device (not shown).

The assemblies of FIGS. 6 and 7 may be manually operated by conventional proximal assemblies (not shown), such as three-ring actuators, pistol grips, or any other actuator which permits linear movement of the rod 74 or cable 82. The devices of FIGS. 6 and 7 would be particularly useful for laparoscopic, thoracoscopic, arthroscopic, or other procedures where they are to be introduced through narrow diameter cannulas, typically having shaft diameters below 12 mm, more typically below 10 mm, and sometimes 5 mm or smaller.

Figure 1B:
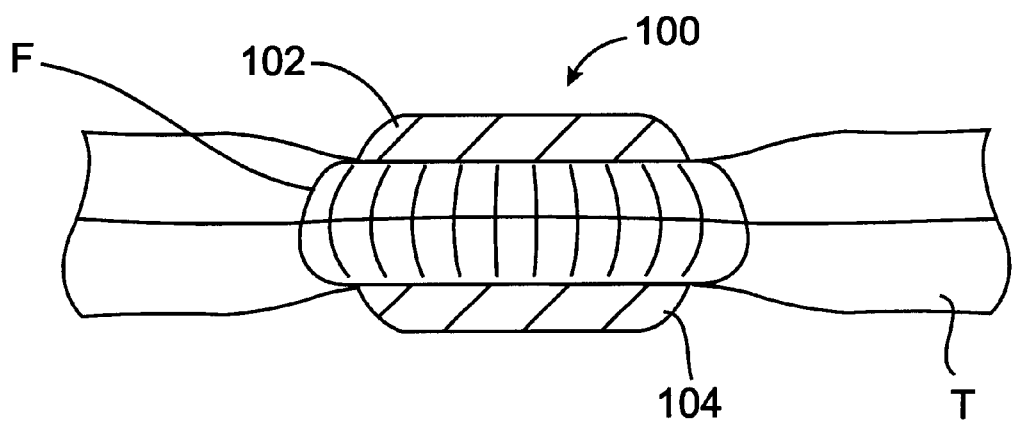
Figure 8:
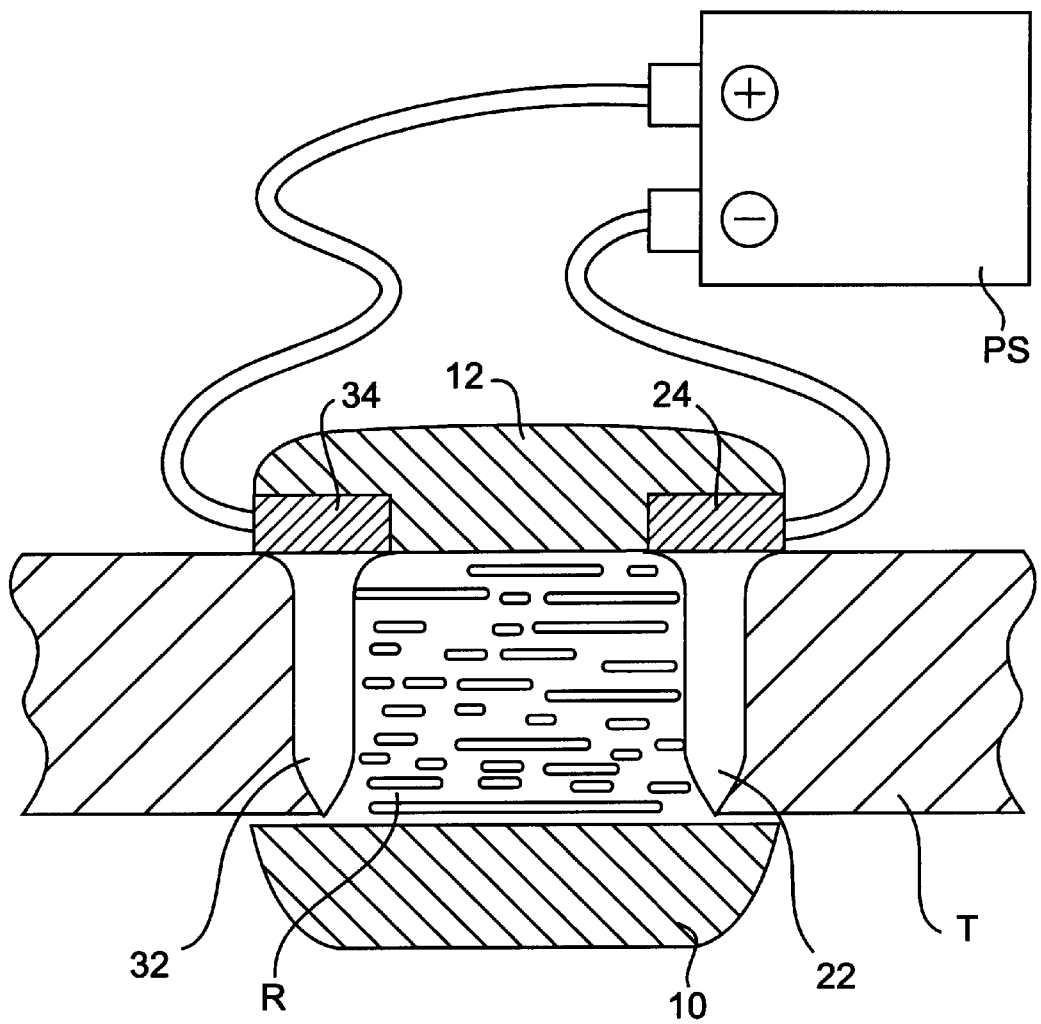
FIG. 8 illustrates use of the jaws of FIG. 1 in treating tissue according to the method of the present invention.

Referring now to FIG. 8, use of the jaws 10 and 12 of FIGS. 1–3 for treating tissue T is illustrated. The jaws 10 and 12 are actuated to grasp a tissue structure, such as an artery, vein, fallopian tube, ligament, or other tubular or elongate structure therebetween. The tissue-penetrating elements 22 and 32 pierce and penetrate into the tissue T to create a region R therebetween. The electrically conductive strips 24 and 34 are attached to an external power supply PS so that they may be energized with opposite polarities. Suitable power supplies are available from commercial suppliers, such as Valleylab, Aspen, and Bovie. The power supplies may operate with conventional sinusoidal or non-sinusoidal wave forms and may operate at fixed or controlled power levels, where voltage, current, or both may be selected. When energized at the power levels, frequencies, and durations described above, the tissue region R between the lines of penetrating elements 22 and 32 will receive a high flux of energy, causing heating, coagulation, and optionally necrosis of the tissue. Heating of the adjacent tissues outside of this region R is minimal.

Figure 9A:
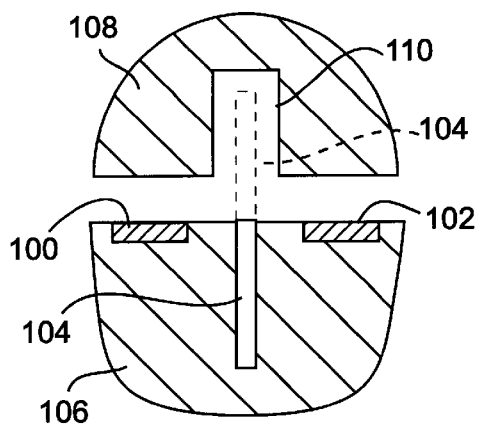
FIGS. 9A–9F illustrate a plurality of alternative reciprocating electrode configurations according to the present invention.
Figure 9B:
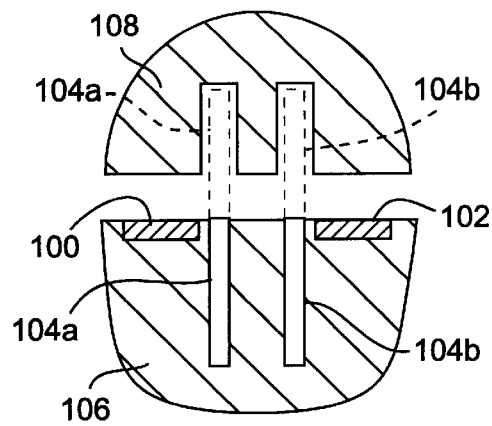
Figure 9C:
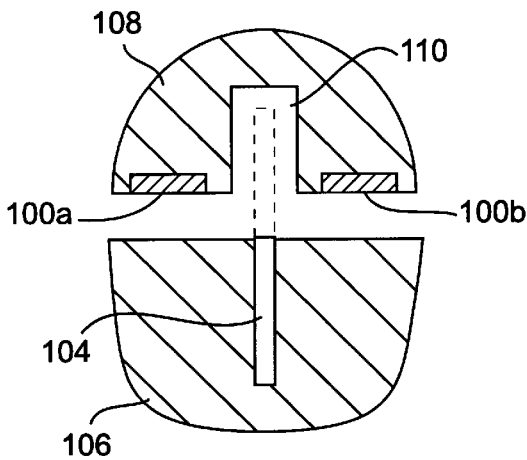
Figure 9D:
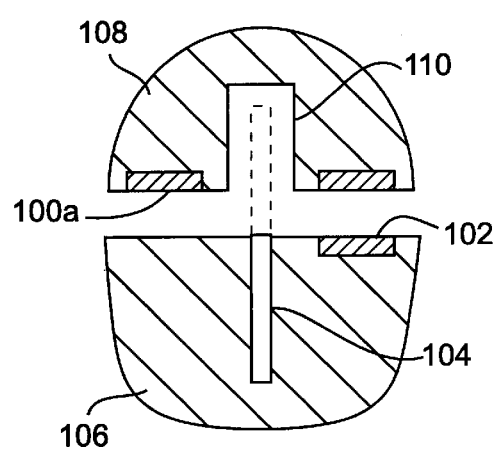
Figure 9E:
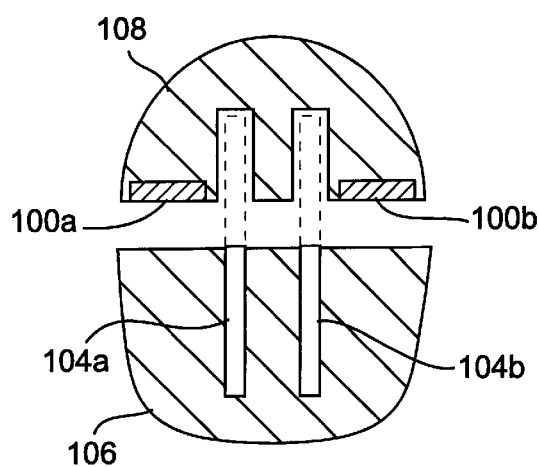
Figure 9F:
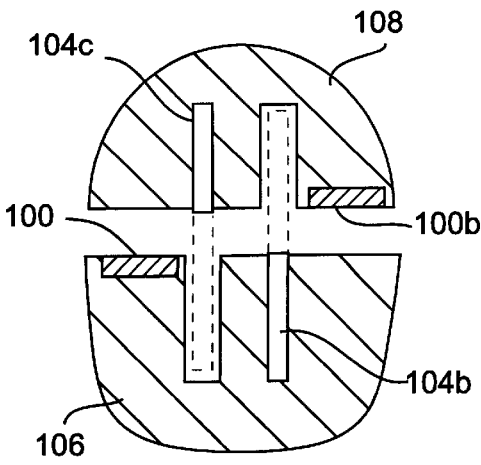

Referring now to FIGS. 9A–9F further electrode configurations will be described. In particular, at least some of the electrode structures may include or consist of a line of tissue-penetrating elements, usually in combination with non-penetrating surface electrodes. Preferably, a pair of laterally spaced-apart elongate surface (non-penetrating) electrodes 100 and 102 will be disposed on opposite sides of a line of reciprocating tissue-penetrating elements 104, as illustrated in FIG. 9A. FIG. 9A is a cross-sectional view where only a single tissue-penetrating element is illustrated. It will be appreciated that a plurality of elements are formed in a line down the length of jaw 106. Similarly, the elongate electrodes 100 and 102 extend along the length of the jaw. An upper jaw 108 is provided to permit tissue clamping, and a channel 10 is formed in the upper jaw to accommodate penetration of the elements 104, as shown in broken line. FIG. 9B illustrates an instrument similar to that shown in FIG. 9A, except that there are two lines 104a and 104b of tissue-penetrating elements positioned between the elongate surface electrodes 100 and 102. The configuration of the instrument shown in FIG. 9C is also similar to that of FIG. 9A, except that the elongate surface electrodes 100a and 100b have been moved to the upper jaw structure 108. FIG. 9 illustrates yet another configuration where a first elongate surface electrode 100a is on the upper jaw structure 108 and a second elongate surface electrode 102 is on the lower jaw structure 106. FIGS. 9E and 9F illustrate instrument configurations having a pair of tissue-penetrating element lines. In FIG. 9E, the lines 104a and 104b are disposed in the lower jaw structure 106, while the elongate surface electrodes 100a and 100b are in the upper jaw structure 108. FIG. 9F illustrates a configuration where a first elongate surface electrode and a second line 104b of tissue-penetrating elements are in the lower jaw structure 106 while a second elongate surface electrode 100b and a first line 104c of tissue-penetrating elements are in the upper jaw structure 108.

As can be seen from above, the relative positions of reciprocating (and non-reciprocatinig) tissue-penetrating elements and elongate surface electrodes (non-penetrating electrodes) can vary widely. In addition, the numbers of elements provided on any surgical instrument can also vary. At a minimum, there will be at least one line of tissue-penetrating elements and one other electrode structure, either tissue penetrating or tissue non-penetrating. The two electrode structures will be elongate, i.e., will have a minimum length dimension of at least 1 mm, more usually being in the range from 5 mm to 25 mm. In the illustrated embodiments, the electrode structures are shown as being generally linear. Other configurations will also be possible, such as concentric, non-linear, serpentine, or the like. The lateral distance between parallel electrode lines, however, will generally remain constant, typically being in the range from 0.5 mm to 10 mm, more usually from 1 mm to 5 mm. The dimensions of the tissue-penetrating elements have been set forth above. The elongate surface electrodes will typically have widths in the range from 0.1 mm to 5 mm, preferably from 0.5 mm to 3 mm. While the surface electrodes are illustrated as being flat, it is also possible that they would have irregular surfaces, possibly to improve electrical contact. The surface irregularities, however, should be such that there is little or no tissue penetration since it is a purpose of the outer surface electrode structures to seal the edges of the tissue being treated and to avoid possible bleeding which could be caused by the introduction of the tissue-penetrating elements.

Figure 10A:
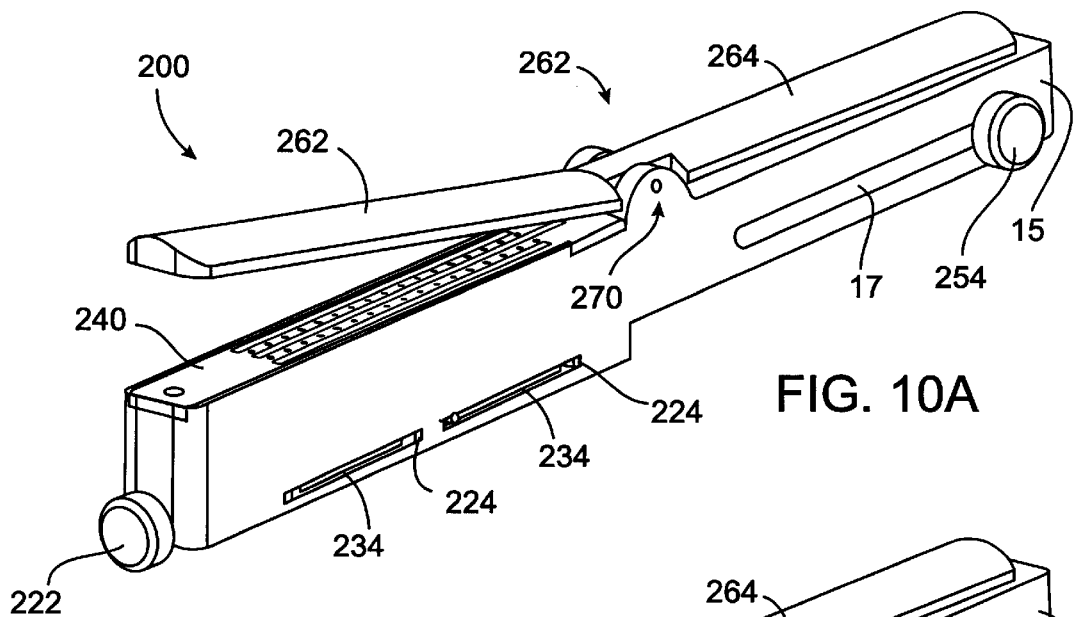
FIGS. 10A–10C illustrate an exemplary bipolar surgical instrument constructed in accordance with the principals of the present invention and employing reciprocating electrode lines.
Figure 10B:
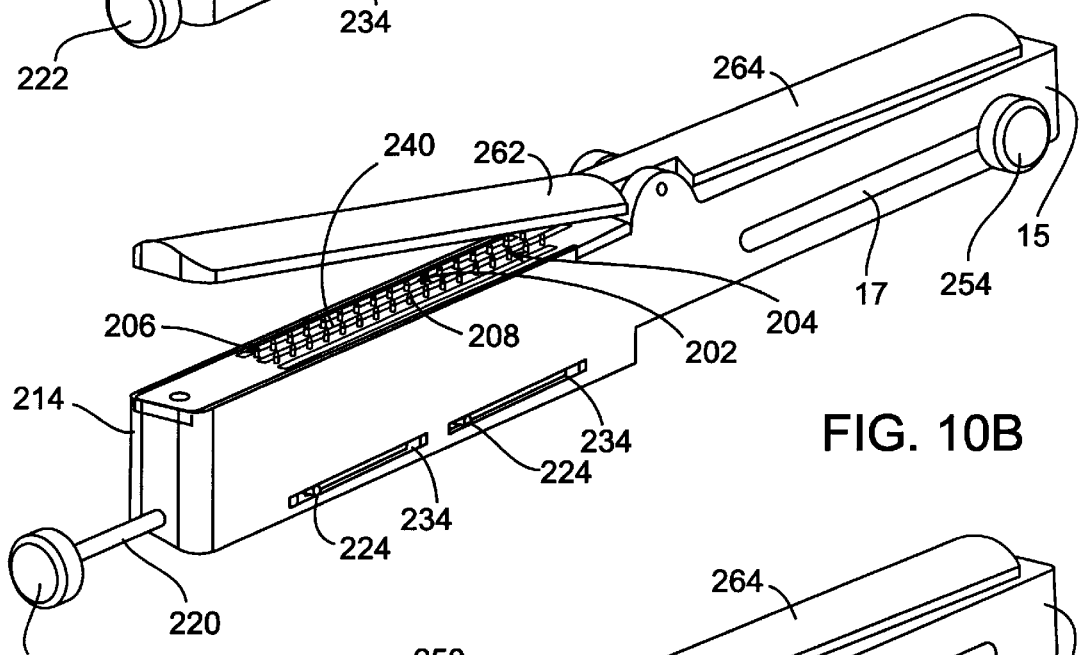

Referring now to FIGS. 10A–10C, 11, 12A, 12B, and 13, a bipolar surgical instrument 200 having an arrangement of surface electrodes 202 and 204 and tissue-penetrating electrodes and lines 206 and 208 of tissue-penetrating electrodes, is illustrated. In lines 206 and 208 of tissue-penetrating electrodes are mounted in an electrically conductive insert 210 (FIG. 13) which in turn is mounted in a cavity 212 in instrument housing 214. The insert 210 is free to reciprocate within the cavity 212 and is mounted on a rod 220 having a knob 222 and a pair of pins 224. The rod 220 is received in a channel 230 in the bottom of insert 210, and the pins 224 extend outwardly through a pair of inclined slots 232 in the insert and then through slots 234 in the side of the housing 214. In this way, axial movement of the rod 220 (caused by pulling or pushing on the knob 222) can cause the insert 210 to rise or lower within the cavity 212. In turn, this causes the tissue-penetrating electrodes 206 and 208 to reciprocate between a lowered configuration (FIG. 10A) and a raised configuration (FIG. 10B).

Figure 10C:
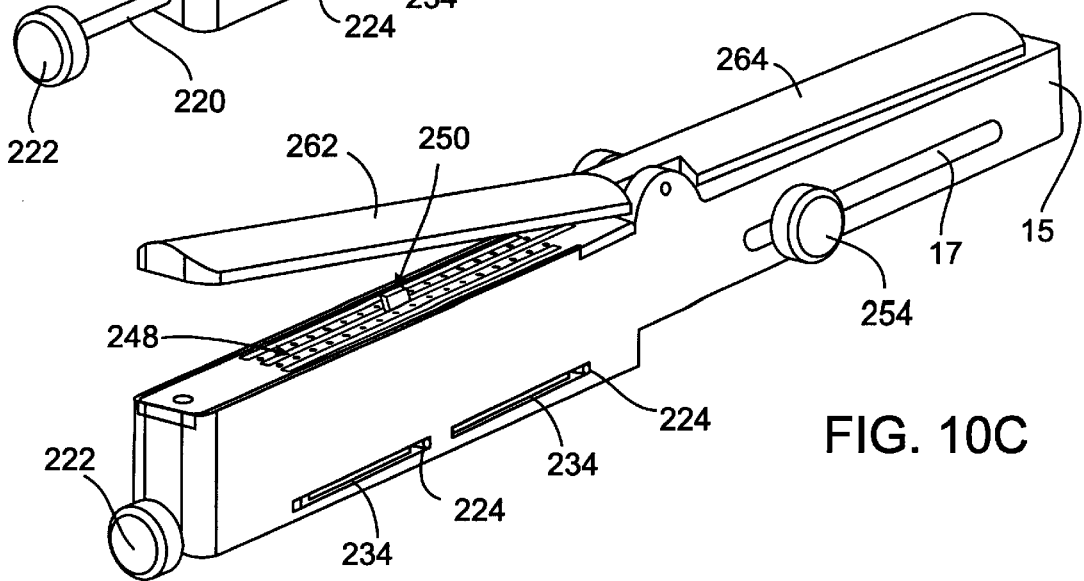

The elongate surface electrodes 202 and 204 are received in an electrically insulating plate 240 which is mounted over the cavity 212 in housing 214. The plate 240 has a pair of slots 242 and 244 for receiving the electrodes 202 and 204, respectively. Additionally, plate 240 has a plurality of holes 246 along the lines spaced inwardly from the slots 242 and 244, respectively. Additionally, a channel 248 is formed along the center line of the plate 240 to receive a cutting blade 250, as best seen in FIG. 10C.

Figure 11:
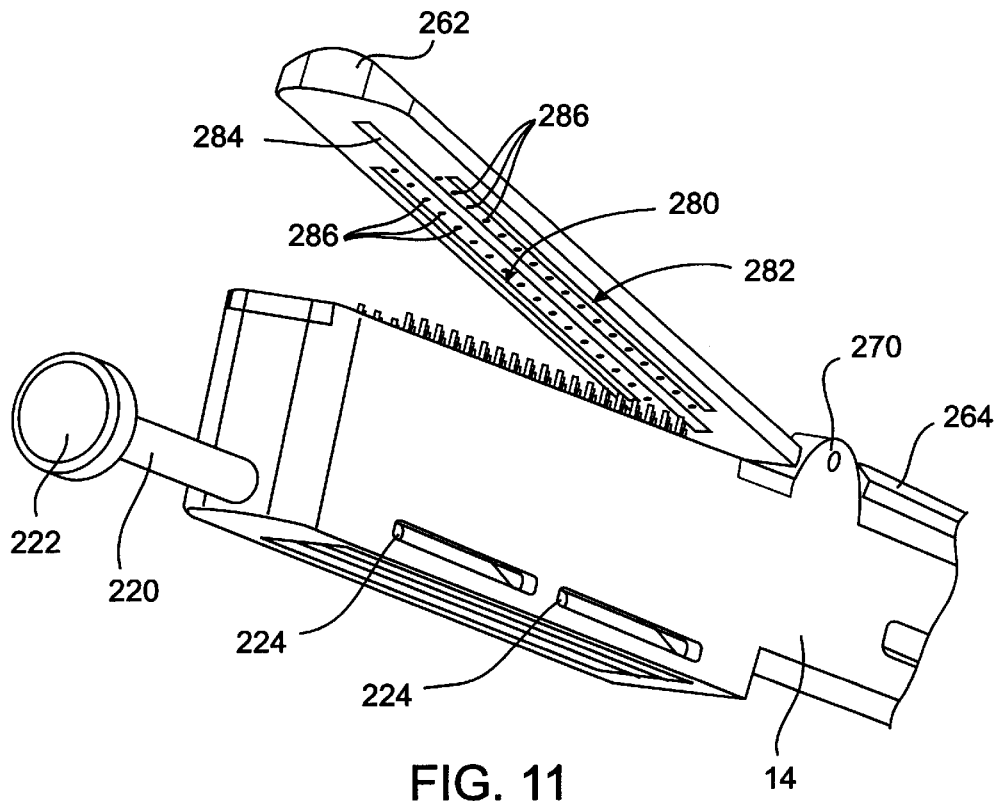
FIG. 11 is an alternative view of the device of FIGS. 10A–10C.

The housing 214 forms a lower jaw structure and a hinged lever assembly 260 forms the upper jaw structure. The lever 260 includes a cover section 262 and a lever arm section 264. A center or fulcrum section 266 is secured between brackets 270 formed on the top of housing 214. In this way, the cover section 262 can be moved between an open configuration (FIG. 10A) and a closed configuration (FIGS. 14B and 14C) by lifting and lowering the lever arm section 264. The bottom of the cover section 262 is best illustrated in FIG. 11. The bottom includes a pair of top surface electrodes 280 and 282, a relief channel 284 for receiving the cutting blade 250, and relief holes 286 for receiving the upper tips of the tissue-penetrating electrodes when they are raised.

The cutting blade 250 is formed at a forward end of an elongate blade structure 252 having a pair of knobs 254 at its opposite or proximal end. The body portion 252 of the blade is received in a slot 258 in a handle portion 15 of the housing 14. The knobs extend on a connecting shaft out through a slot 17 in the handle 15. Thus, the blade can be advanced and retracted axially by moving the knob 254 from a retracted configuration (FIGS. 10A and 10B) to an advanced configuration (FIG. 10C). The knob is disposed in the channel 248 so that it will pass and cut through tissue which has been previously necrosed by applying high frequency energy through the electrode structures, as described below.

Figure 12A:
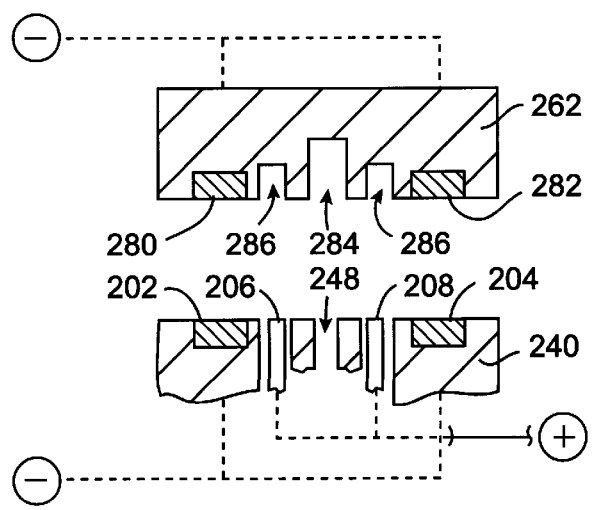
FIGS. 12A and 12B illustrate the relative positions of the various electrode structures in the device of FIGS. 10A–10C.
Figure 12B:
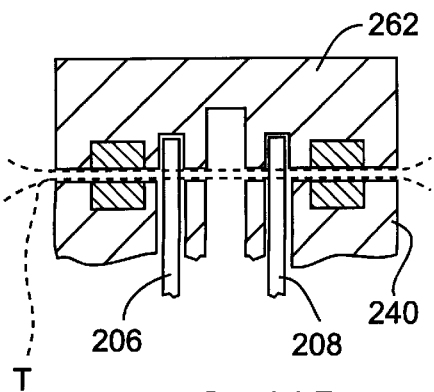
Figure 13:
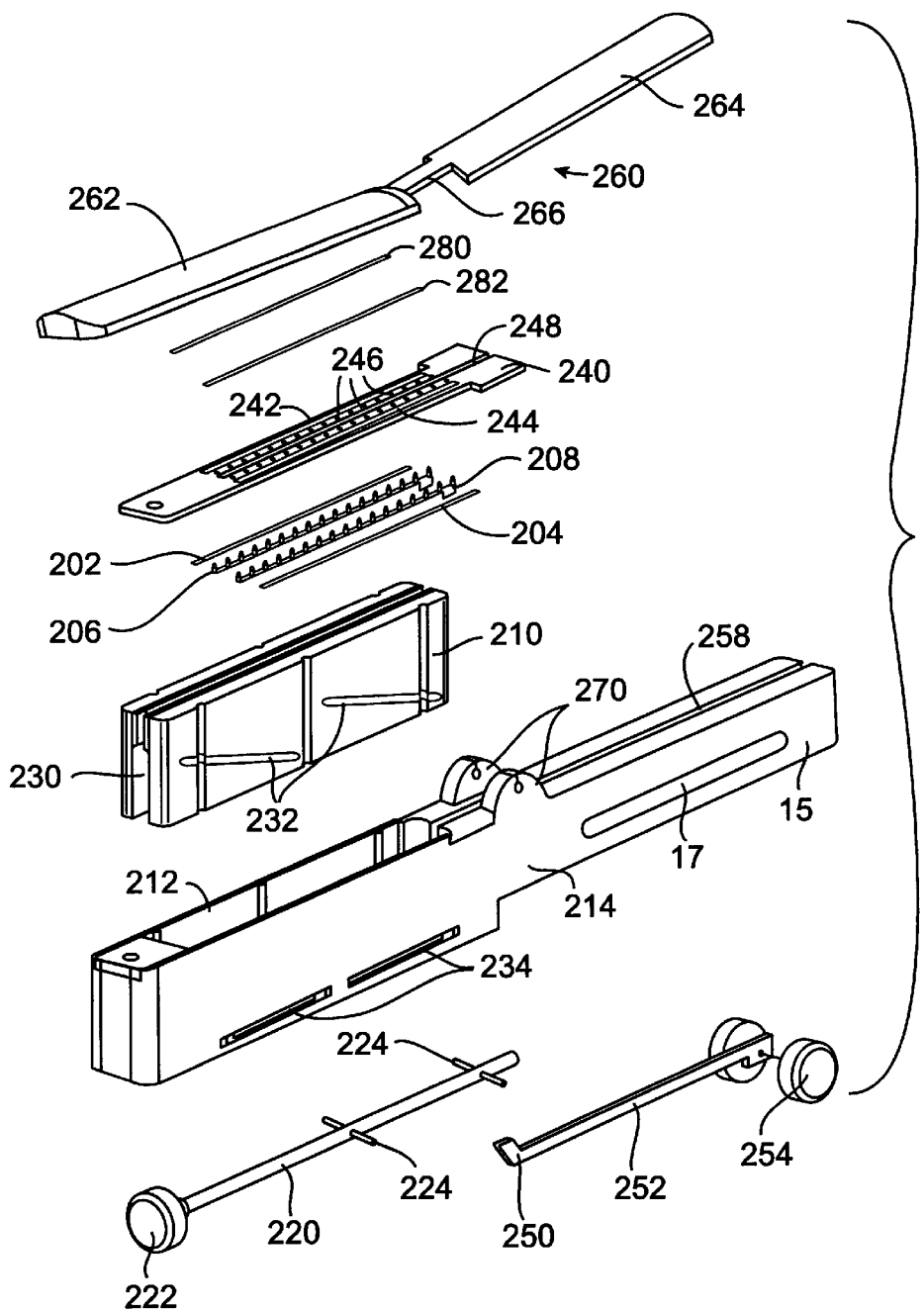
FIG. 13 is an exploded view of the device of FIGS. 10A–10C.
Figure 14A:
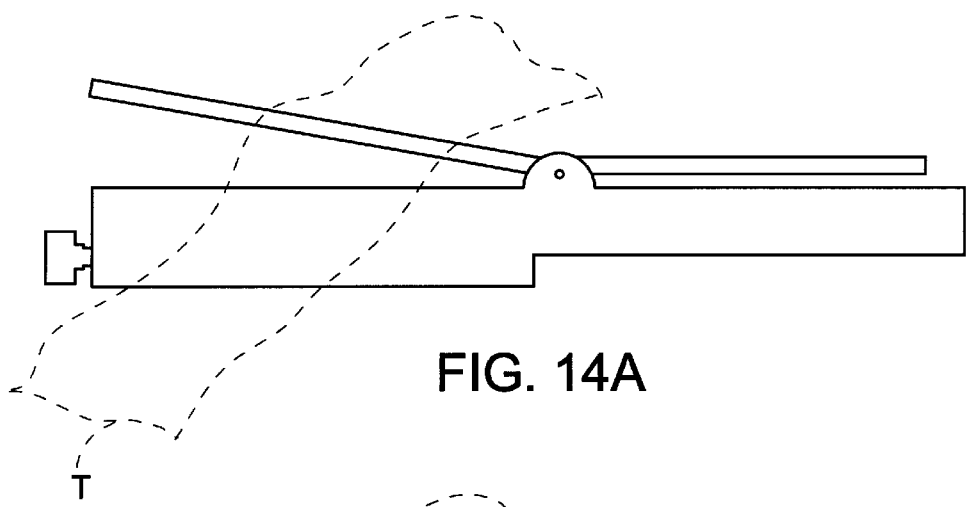
FIGS. 14A–14C illustrate use of the device of FIGS. 10A–10C in applying high frequency electrical energy to tissue.
Figure 14B:
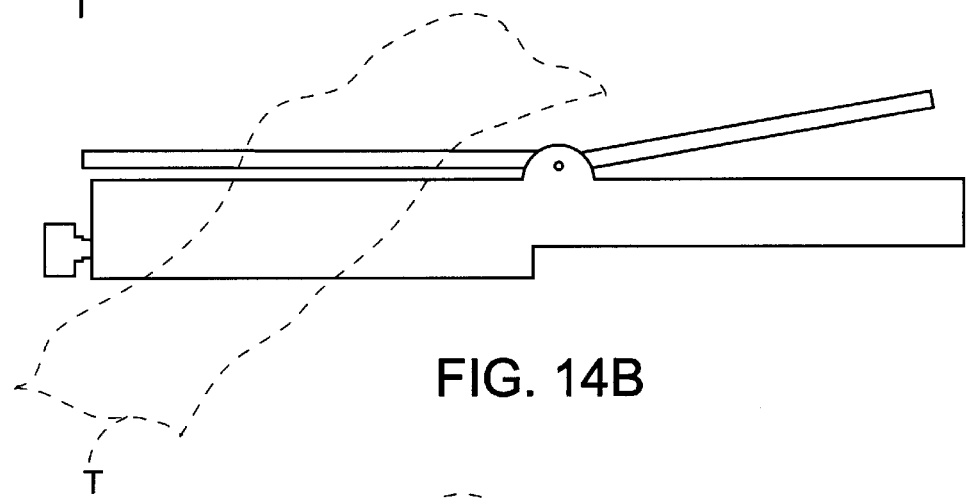
Figure 14C:
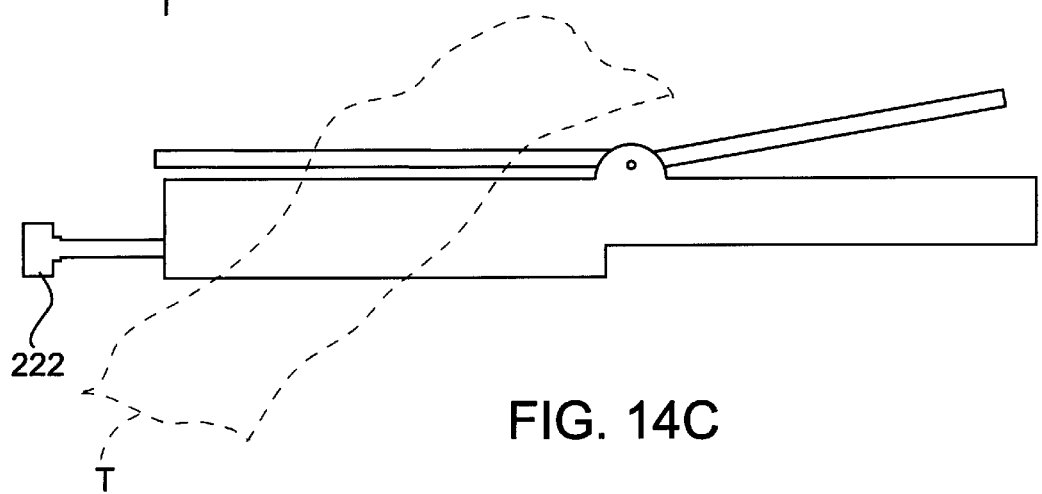

Referring now to FIGS. 12A and 12B, the interrelationship of the various electrode structures and instrument 200 will be described. Initially, the cover 262 will be open and the tissue-penetrating electrodes 206 and 208 retracted into the housing 14, as shown in FIG. 12A. After positioning a target tissue structure between the open cover 262 and plate 240 of the housing 14 (as shown in FIG. 14A), the cover can be closed capturing the tissue (as shown in FIGS. 12B and 14B). The tissue-penetrating electrodes are then raised by pulling knob 222 (FIGS. 12B and 14C), causing the electrodes 206 and 208 to penetrate the tissue. Surface electrodes 202, 204, 280, and 282 in contrast, will compress on opposite sides of the tissue, but will not penetrate into the tissue. Radiofrequency or other high frequency electrical energy will then be applied to the tissue, with the surface electrodes being attached to one pole of a suitable power supply and the tissue-penetrating electrodes being attached to the other pole. The electrical field will thus be concentrated between an outermost pair of surface electrodes (202/280 or 204/282) and the adjacent tissue-penetrating electrode (206 or 208). The tissue may be fully necrosed with all the advantages of the use of a tissue-penetrating electrode as described above. After adequate necrosis is achieved, the blade 252 can be advanced to cut through the parallel segments of necrosed tissue which have been formed.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A bipolar surgical instrument comprising:
   a shaft having a proximal end and a distal end;
   a pair of opposed jaws at the distal end of the shaft;
   a first electrode member on one of the jaws;
   a second electrode member on one of the jaws, wherein the first and second electrode members are electrically isolated from each other; and
   an actuating mechanism for moving the jaws between an opened and closed configuration, wherein electrode members lie parallel to and laterally spaced-apart from each other when the jaws are closed and wherein at least one of the electrode members comprises a plurality of tissue-penetrating elements which project toward the opposed jaw.

2. A bipolar surgical instrument as in claim 1, wherein the electrode members are laterally spaced-apart by a distance in the range from 0.5 mm to 10 mm.

3. A bipolar surgical instrument as in claim 1, wherein the electrode members have a length in the range from 1 mm to 50 mm.

4. A bipolar surgical instrument as in claim 1, wherein electrode members are on the same jaw.

5. A bipolar surgical instrument as in claim 1, wherein the first electrode member is on one jaw and the second electrode member is on the other jaw.

6. A bipolar surgical instrument as in claim 1, wherein both electrode members comprise a plurality of tissue-penetrating elements which project toward the opposed jaw.

7. A bipolar surgical instrument as in claim 1, wherein the tissue-penetrating elements have a length in the range from 1 mm to 10 mm and a diameter in the range from 0.1 mm to 2 mm.

8. A bipolar surgical instrument as in claim 7, wherein the first and second electrode members each comprise from 3 to 50 penetrating elements.

9. A bipolar surgical instrument as in claim 8, wherein the tissue-penetrating elements are arranged in two straight lines which are parallel to each other when the jaws are closed over tissue.

10. A bipolar surgical instrument as in claim 1, further comprising a third electrode member aligned with the first electrode member but disposed on the other jaw and a fourth electrode member aligned with the second electrode member but disposed on the other jaw.

11. A bipolar surgical instrument as in claim 1, wherein at least one of the jaws is perforated to permit the release of steam during use.

12. A bipolar surgical instrument as in claim 1, wherein the actuating mechanism comprises scissors, a camming mechanism, or a linear/pivot actuator.

13. A method for applying high frequency electrical energy to tissue, said method comprising:
    grasping tissue between first jaw and a second jaw;
    applying high frequency energy between a first electrode member on one of said jaws and a second electrode member on one of said jaws, wherein said lines of tissue-penetrating elements are parallel to and laterally spaced-apart from each other when grasping the tissue wherein at least one of the electrode members comprises a plurality of tissue-penetrating elements which project toward the opposed jaw.

14. A method as in claim 13, further comprising penetrating a plurality of tissue-penetrating elements into the tissue, wherein said tissue-penetrating elements are electrically coupled to and part of at least one of the electrodes.

15. A method as in claim 13, wherein the high frequency energy is applied at a level and for a time sufficient to necrose substantially all tissue between said electrode members without causing substantial damage to other tissue.

16. A method as in claim 15, wherein the high frequency energy has a frequency from 100 kHz to 2 MHz, a power level from 25 W to 250 W, and is applied for a time from 5 seconds to 5 minutes.

17. A method as in claim 13, wherein the electrode members are laterally spaced-apart by a distance in the range from 0.5 mm to 10 mm.

18. A method as in claim 13, wherein the electrode members have a length in the range from 1 mm to 50 mm.

19. A method as in claim 13, wherein both electrode members are on the same jaw.

20. A method as in claim 13, wherein the first electrode member is on one jaw and the second electrode member is on the other jaw.

21. A method as in claim 20, wherein the tissue-penetrating elements have a length from 1 mm to 10 mm and a diameter in the range from 0.1 mm to 2 mm.

22. A method as in claim 13, wherein the first and second electrode members each comprise from 5 to 50 penetrating elements.

23. A methods as in claim 13, wherein the tissue-penetrating elements are arranged in two straight lines which are parallel to each other when the jaws are closed over the tissue.

24. A methods as in claim 13, wherein the energy is further applied between a third electrode member aligned with the first electrode member but disposed on the other jaw and a fourth electrode member aligned with the second electrode member but disposed on the other jaw.

25. A method as in claim 13, wherein at least one of the jaws is perforated to permit the release of steam during use.

26. A bipolar surgical instrument comprising:
    a shaft having a proximal end and a distal end;
    a pair of opposed jaws at the distal end of the shaft;
    at least two laterally spaced-apart elongate surface electrodes on the jaws;
    at least a first line of tissue-penetrating elements on the jaws, wherein the first line of electrodes is arranged to lie between the surface electrodes when the jaws are closed; and
    an actuator for opening and closing the jaws.

27. A bipolar surgical instrument as in claim 26, wherein the tissue-penetrating elements are retractable relative to a surface of the jaw.

28. A bipolar surgical instrument as in claim 27, further comprising means for selectively advancing at least some of the tissue-penetrating electrodes relative to at least one of the jaws.

29. A bipolar surgical instrument as in claim 26, further comprising:
   at least a second line of tissue-penetrating elements on the jaws.

30. A bipolar surgical instrument as in claim 24, wherein the first and second lines of tissue-penetrating elements are on the same jaw.

31. A bipolar surgical instrument as in claim 24, wherein the first and second lines of tissue-penetrating elements are on different jaws.

32. A bipolar surgical instrument as in claim 26, further comprising an actuable cutting blade disposed to cut along a line between the first and second lines of tissue-penetrating elements.

33. A method for applying high frequency energy to tissue, said method comprising:
   contacting a tissue region with at least two laterally spaced-apart elongate surface electrodes;
   penetrating at least a first line of tissue-penetrating elements through a surface over the tissue region between the laterally spaced-apart surface electrodes; and
   applying bipolar high frequency electrical energy between the surface electrodes and the tissue-penetrating elements.

34. A method as in claim 33, further comprising penetrating at least a second line of tissue-penetrating elements through a tissue surface into tissue between the first line of tissue-penetrating elements and one of the surface electrodes.

35. A method as in claim 34, wherein the contacting and the penetrating are performed sequentially.

36. A method as in claim 34, wherein the contacting and the penetrating are performed simultaneously.

37. A method as in claim 33, wherein the surface electrodes are contacted against a common tissue surface over the tissue region.

38. A method as in claim 37, wherein the common tissue surface is the same as the tissue surface through which the first line of penetrating elements is penetrated.

39. A method as in claim 37, wherein the common tissue surface is opposed to the tissue surface through which the first line of penetrating elements is penetrated.

40. A method as in claim 33, wherein a first of the laterally spaced-apart surface electrodes is contacted the tissue surface through which the tissue-penetrating elements are penetrated and a second of the laterally spaced-apart surface electrodes is contacted against an opposed tissue surface.

* * * * *

UNITED STATES PATENT AND TRADEMARK OFFICE
CERTIFICATE OF CORRECTION

PATENT NO. : 6,162,220
DATED : December 19, 2000
INVENTOR(S) : Nezhat, Camran

It is certified that error appears in the above-identified patent and that said Letters Patent is hereby corrected as shown below:

Column 11,
Line 31, after "jaw" insert -- , wherein at least some of the tissue-penetrating elements are retractable relative to a surface of the jaw upon which they are mounted --.

Column 12,
Line 3, after "between" insert -- a --;
Lines 5 and 6, after "member" insert -- comprising a line of tissue-penetrating elements --.
Line 57, replace "electrodes is" with -- tissue-penetrating elements are --.

Column 14,
Line 20, after "contacted" insert -- against --.

Signed and Sealed this

Twenty-first Day of May, 2002

*Attest:*

JAMES E. ROGAN
*Attesting Officer*     Director of the United States Patent and Trademark Office